United States Patent [19]
Massie

[11] 3,968,774
[45] July 13, 1976

[54] MASTITIS DETECTOR

[75] Inventor: Kenneth Herbert Massie, Bromborough, England

[73] Assignee: Chalton Electronic Services Limited, Wales

[22] Filed: Mar. 5, 1975

[21] Appl. No.: 555,706

Related U.S. Application Data

[62] Division of Ser. No. 399,613, Sept. 21, 1973, Pat. No. 3,884,187.

[52] U.S. Cl. ............................................ 119/14.14
[51] Int. Cl.² ............................................. A01J 7/00
[58] Field of Search ............ 119/14.14, 14.15, 14.16, 119/14.17, 14.18, 14.05, 14.06

[56] References Cited
UNITED STATES PATENTS
2,997,020   8/1961   Barkman ......................... 119/14.18

3,841,756   10/1974   Grochowicz ................. 119/14.17 X

FOREIGN PATENTS OR APPLICATIONS
615,692   3/1961   Canada ............................ 119/14.14

*Primary Examiner*—Hugh R. Chamblee
*Attorney, Agent, or Firm*—Scrivener Parker Scrivener & Clarke

[57] ABSTRACT

A conductivity cell through which milk may be passed, comprising a generally spherical housing having diametrically opposed inlet and outlet ports, a tubular member within said spherical housing, the outer wall of the tubular member and a portion of the inner wall of the housing defining an annular well, two electrodes extending through said housing and having ends spaced apart within said well, and said tubular extension having a duct therethrough connecting said well to one of said ports.

4 Claims, 1 Drawing Figure

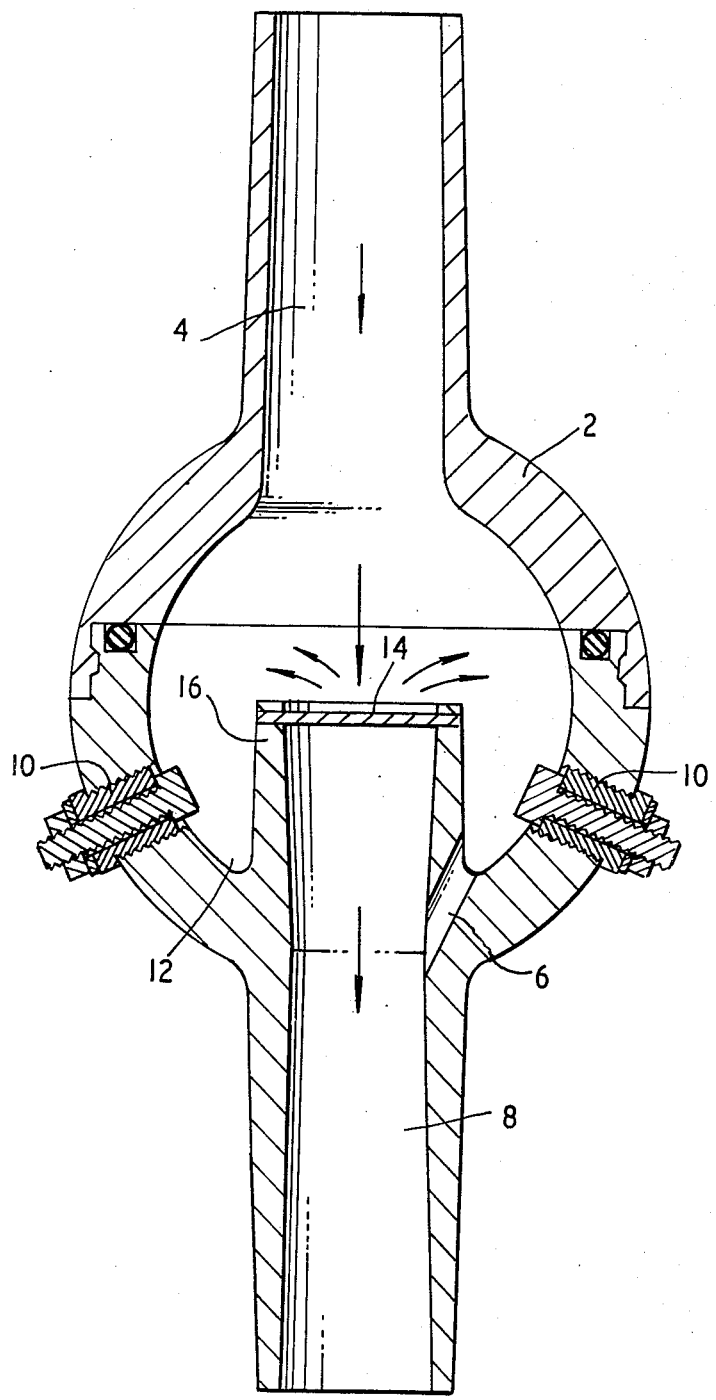

MASTITIS DETECTOR

This application is a Divisional Application out of copending application Ser. No. 399,613, now U.S. Pat. No. 3,884,187, for which I am one of the applicants.

The invention relates to cells and in particular to a cell for measuring the conductivity of cow's milk.

The present invention provides a cell suitable for use with the milk conductivity indicating apparatus in the said co-pending application Ser. No. 399,613.

According to the present invention there is provided a cell comprising a casing defined by a generally spherical wall having diametrically opposed inlet and outlet ports, a tubular member within said spherical wall, the outer wall of the tubular member and a portion of the inner wall of the spherical wall defining an annular well, two electrodes extending through said spherical wall and having ends spaced apart within said well, and said tubular member having a duct therethrough connecting said well to one of said ports.

Advantageously, the conductivity cell is manufactured from polycarbonate and has a smooth finish to the interior, the shape and construction substantially avoiding restriction to milk flow therethrough and to retained contaminents for future milk. This substantially reduces the lodging and growth of bacteria in the interior of the cell.

Preferably the cell electrodes are manufactured from high purity hard graphite.

The invention is further described, by way of example, with reference to the accompanying drawing which is a longitudinal sectional view of a milk conductivity cell according to the present invention.

Referring to the drawing a milk conductivity cell is manufactured from polycarbonate. The wall 2 of the cell is generally spherical and has a smooth finish to the interior, the shape and construction substantially avoiding restriction to milk flow therethrough and to retained contaminants for future milking.

The cell is situated at the inlet to a measuring jar (not shown) directly coupled in the milk flow line from the teat cup cluster of a milking machine.

A port 8 of the cell has a cylindrical extension 16 which extends inwardly towards the interior of the cell so defining an annular well 12 between the outside wall face of the extension 16 and a portion of the inside wall face of the cell.

Two electrodes 10 are manufactured from high purity hard graphite, each electrode being ¼ inch in diameter and protruding into the well 12 through the conductivity cell wall 2 by ⅛ inch. The terminals of the electrodes are exterior to the cell wall and comprise a stainless screw inserted into the graphite.

During a milking period the milk enters the conductivity cell via the port 8 and leaves the cell via a port 4. Splash back fills the well 12 with a sample of the milk to be tested and the conductivity of the milk sample between the electrodes 10 which are submerged therein can then be measured. A drain opening 6 serves to drain back to the port 8 the milk sample which has accumulated in the well 12 but is dimensioned to be sufficiently small to retain the sample in the well during measurement. Thus, the cell is cleared of milk so that it is ready to test the next milk sample. This process is repeated at a frequency determined by the frequency determined by the frequency of the vacuum pulsations at which the milking machine operates.

The cell can alternatively be arranged so that the milk flows through the cell in the opposite direction to that described above. Thus, the milk enters the conductivity cell via the port 4 and leaves via the port 8. Splash back of the milk is created by an adapter bar 14 which is fitted across the end of the extension 16. The splash back causes the flling of the well 12 and enables sampling to take place. The milk sample accumulated in the well 12 drains through the drain opening 6.

To simplify manufacture of the cell, the elelctrodes 10 may be arranged to enter the cell wall 2 through suitable bosses in directions parallel to the longitudinal axis rather than radially as illustrated.

The shape of the cell and the materials from which it is manufactured enable the cell to be kept in a high state of cleanliness and to be sterilized regularly.

We claim:

1. A cell comprising a casing defined by a generally spherical wall having diametrically opposed inlet and outlet ports, a tubular member within said spherical wall and forming an extension to one of said ports, the outer wall of the tubular member and a portion of the inner wall of the spherical wall defining an annular well, to receive a sample of milk flowing into the cell through said inlet port, and two electrodes extending through said spherical wall and having ends spaced apart within said well, said tubular member having a drainage duct therethrough connecting said well to said one of said ports, said duct having dimensions such as to retain said milk sample in said well with said electrodes submerged therein.

2. A cell according to claim 1 in which said casing and tubular member comprise polycarbonate and define a smooth finish to the interior of said casing.

3. A cell according to claim 1 in which said electrodes comprise high purity hard graphite.

4. A cell according to claim 1 in which said casing consists of two substantially hemispherical parts provided respectively with one of said inlet and outet ports and means for releasably and sealingly joining said parts together, said tubular member being formed concentrically with the one of said hemispherical parts provided with said one port.

* * * * *